US00PP16002P3

(12) United States Plant Patent
Brits

(10) Patent No.: US PP16,002 P3
(45) Date of Patent: Sep. 27, 2005

(54) ***PLECTRANTHUS* PLANT NAMED 'P000603'**

(50) Latin Name: *Plectranthus hybrida*
Varietal Denomination: P000603

(76) Inventor: Gert Johannes Brits, 28, Flamingo Rd., ZA-7600 Stellenbosch (ZA)

( * ) Notice: Subject to any disclaimer, the term of this patent is extended or adjusted under 35 U.S.C. 154(b) by 0 days.

(21) Appl. No.: 10/716,659

(22) Filed: Nov. 20, 2003

(65) Prior Publication Data

US 2005/0114972 P1 May 26, 2005

(51) Int. Cl.[7] ..... A01H 5/00
(52) U.S. Cl. ..... Plt./263
(58) Field of Search ..... Plt./263, 373

(56) References Cited

PUBLICATIONS

UPOV–ROM GTITM Plant Variety Database, 2004/02, GTI Jouve Retrieval Software, Citation for *Plectranthus* 'P000306'.*
UPOV–ROM GTITM Plant Variety Database, 2004/02, GTI Jouve Retrieval Software, Citation for *Plectranthus* 'P000603'.*

* cited by examiner

*Primary Examiner*—Anne Marie Grunberg
*Assistant Examiner*—June Hwu
(74) *Attorney, Agent, or Firm*—Foley & Lardner, LLP

(57) ABSTRACT

A new and distinct cultivar of *Plectranthus* plant named 'P000603', characterized by having more compact, freely branching plant habit; shorter production time; vigorous growth habit; light pink flowers; and dense colorful foliage.

2 Drawing Sheets

Latin name of genus and species of the plant claimed: *Plectranthus hybrida*.
Variety denomination: P000603.

BACKGROUND OF THE INVENTION

The present invention relates to a new and distinct cultivar of *Plectranthus* plant, botanically known as *Plectranthus hybrida* (Family Lamiaceae), hereinafter referred to by the name 'P000603'.

The new *Plectranthus*, 'P000603', is a product of a planned breeding program conducted by the Inventor, Gert Johannes Brits, in Stellenbosch, Republic of South Africa. The objective of the breeding program is to improve upon the *Plectranthus* varieties currently available, such as the cultivar 'Edelbau' (unpatented) by developing a *Plectranthus* variety with more compact growth habit, larger flowers and improved vigor.

The new *Plectranthus* originated from a hybrid backcross by the Inventor between a proprietary selection of a *Plectranthus* hybridnamed 'F1' (*Plectranthus saccatus*×*P. hilliardiae*; unpatented) and a proprietary selection of unnamed *Plectranthus hilliardiae* (unpatented). The parental cultivar, *P. hilliardiae*, has a compact plant habit, large elongated leaves, purple veined leaves on the underside, and a narrow, elongated flower tube. The parent cultivar *Plectranthus* hybrid named 'F1' has a tall, straggly plant habit, the leaves are not elongated, green leaves on the underside, and large, wide flower tube, largest flower in the genus. The Inventor selected the new *Plectranthus* cultivar 'P000603' from the progeny of the above cross in 2001 on the basis of its compact growth habit, larger flowers and increased vigor.

Asexual reproduction of the new *Plectranthus* cultivar by vegetative propagation (terminal cuttings) was first performed in March, 2001, in Stellenbosch, South Africa, and has demonstrated that each of the progenies exhibit characteristics identical to the original plant. These characteristics have been shown to come true to form through many generations of asexual propagation under commercial production conditions in Nr. Lyndelse, Fyn, Denmark. The present invention has been tested under lighted greenhouse conditions and for keeping quality in a consumer environment, but may differ in various aspects if grown under different conditions.

SUMMARY OF THE INVENTION

Plants of the cultivar 'P000603' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'P000603'. These characteristics in combination distinguish 'P000603' as a new and distinct cultivar:

1. Light pink flowers;
2. Compact and freely branching plant habit;
3. Shorter production time, 12–14 weeks compared to 16–28 weeks; and
4. Dense, colorful foliage.

Side-by-side comparisons between the instant plant and other similar *Plectranthus* were conducted by the Inventor, including the variety 'Edelblau'. Plants of 'P000603' differs from other similar *Plectranthus* cultivars and the variety 'Edelblau' in the following characteristics:

1. Plants of 'P000603' have larger light pink flowers than plants of similar *Plectranthus* cultivars.
2. Plants of 'P000603' have better branching growth habit and denser, more colorful foliage than plants of similar *Plectranthus* cultivars.
3. Plants of 'P000603' have a faster growth rate than plants of similar *Plectranthus* cultivars.

BRIEF DESCRIPTION OF THE DRAWINGS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of 'P000603'.

The first photographic drawing shows a side perspective view of a typical flowering plant of 'P000603' as grown in 12 cm pots.

The second photographic drawing shows a close-up view of typical flowering racemes of 'P000603'.

DETAILED BOTANICAL DESCRIPTION

In the following description, color references are made to The Royal Horticultural Society (R.H.S.) Colour Chart, $4^{th}$ edition. Plants were grown under greenhouse conditions. The plants described were between 15 and 18 weeks old after cutting, as grown in 12 cm pots.

Parentage: Hybrid backcross between proprietary selection of a *Plectranthus* hybrid named 'F1' (*Plectranthus saccatus*×*P. hilliardiae*; unpatented) and unnamed *Plectranthus hilliardiae* (unpatented).

Propagation: Type cutting. Terminal vegetative cuttings.

Plant description:

*Form.*—Perennial, herbaceous plant with upright, branched plant form.

*Crop time.*—Flowering induced by short day treatment in 12 cm pots for 4 weeks under greenhouse conditions.

*Plant height* (*soil level to top of plant plane*).—About 35 cm.

*Plant spread.*—About 35 cm.

*Stem.*—Upright, stiff, square, branching from base, RHS 136B (dark green).

*Vigor.*—Vigorous growth rate.

*Foliage description.*—Leaves single, ovate, serrate. Arrangement: opposite, decussate. Length: 8 cm. Width: 6 cm. Apex: Acuminate. Base: Cuneate. Texture: adaxial: rough (hispid), shiny; abaxial: smooth, velvety. Venation: prominent, dark purple-brown, N79 B. Color, ventral side: Young foliage, upper and lower surfaces: RHS 136 A, green. Mature foliage, upper and lower surfaces: RHS 136 A. Color, dorsal side: Young foliage, RHS 138 B. Mature foliage: RHS 138 B.

*Petiole.*—3 cm in length, 5 mm in diameter, hispid texture, RHS 147 A.

Flower description:

*Flower arrangement.*—Raceme of panicles

*Flower shape.*—Irregular labiate, flat tubular with 4 lips of different size and shape. .

*Flower longevity on the plant.*—Longevity of individual flowers is highly dependent on temperature and light conditions; single flowers last from 4 to 6 days in the greenhouse with full sun and temperatures not exceeding 20° C.; plant may retain flowers up to 4 weeks in sufficient light and temperatures not exceeding 20° C.

*Number of flowers per inflorescence.*—20; 60 stem; up to 150 per plant.

*Inflorescence size.*—Height: 8 cm; Diameter; 8 cm; average size of individual flower is 22 mm.

*Floral tube.*—Slightly shorter than 22 mm in length; diameter: 11 mm.

*Buds.*—Length: Up to 15 mm before antithesis; height: 5 mm; width: 1 mm; tubular with angular "head", RHS 72 A; base RHS 63 B, pink, to white-purple RHS 72D.

*Pedicel.*—Length: 4 mm; width: 1 mm; texture: slightly glutinous; color: purple, RHS N79A.

*Peduncle.*—Length: 6 mm; width: 3 mm; texture: slightly glutinous; color: purple, RHS N79A.

*Petals.*—5 fused to basal, flat tubular corolla. Lips spotted, velvety texture. Top lip (2 fused) to inverted cordate form, revolute upright, 9 mm. Bottom lip involute, almost cup-shaped, 5 mm. Wing lips small, rounded, 2 mm. Color: ventral side of lips: light purple, RHS 73 B; red-purple spots: N79C; throat: light violet, RHS 85D; dorsal side: light red-purple, RHS 72 C.

*Calyx.*—5 pointed lobes fused at base; veins: dark purple, RHS N79A; ground tissue: green, RHS 138 C.

Reproductive organs:

*Stamen.*—4 monoadelphous, lower part fused to corolla tube; length: 8 mm.

*Anther.*—Kidney-shaped; length: 0.2 mm; color: purple, RHS N79B.

*Filaments.*—Length: 6 mm; color: purple, RHS N79B.

*Pistil.*—One, lower part fused to corolla tube; free part 5 mm, curling upward with cleft sitgma, purple, RHS N79B.

*Ovary.*—RHS N144A, yellow-green.

*Seed.*—No seeds observed.

Fragrance: None.

Weather tolerance: Plants of the new *Plectranthus* have exhibited good tolerance to drought, rain and wind, low temperature resistant to 5° C.

I claim:

1. A new and distinct cultivar of *Plectranthus* plant named 'P000603', as illustrated and described herein.

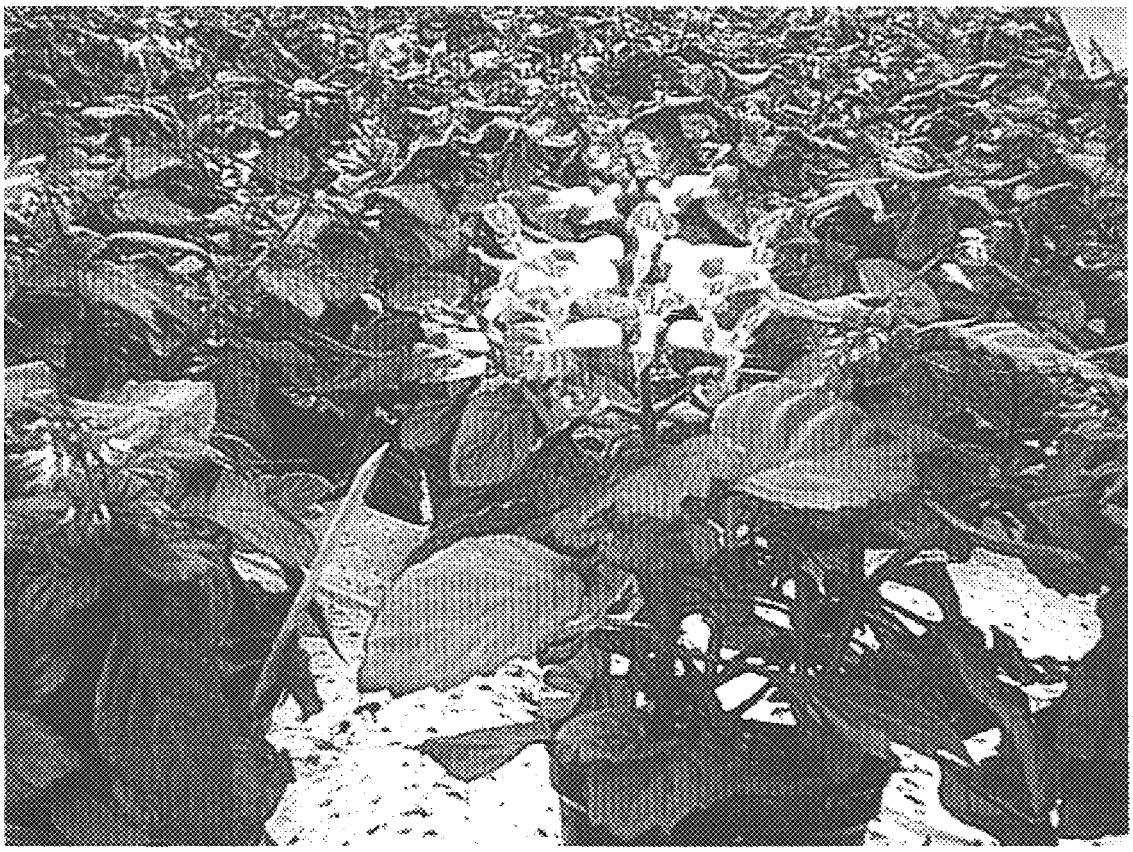

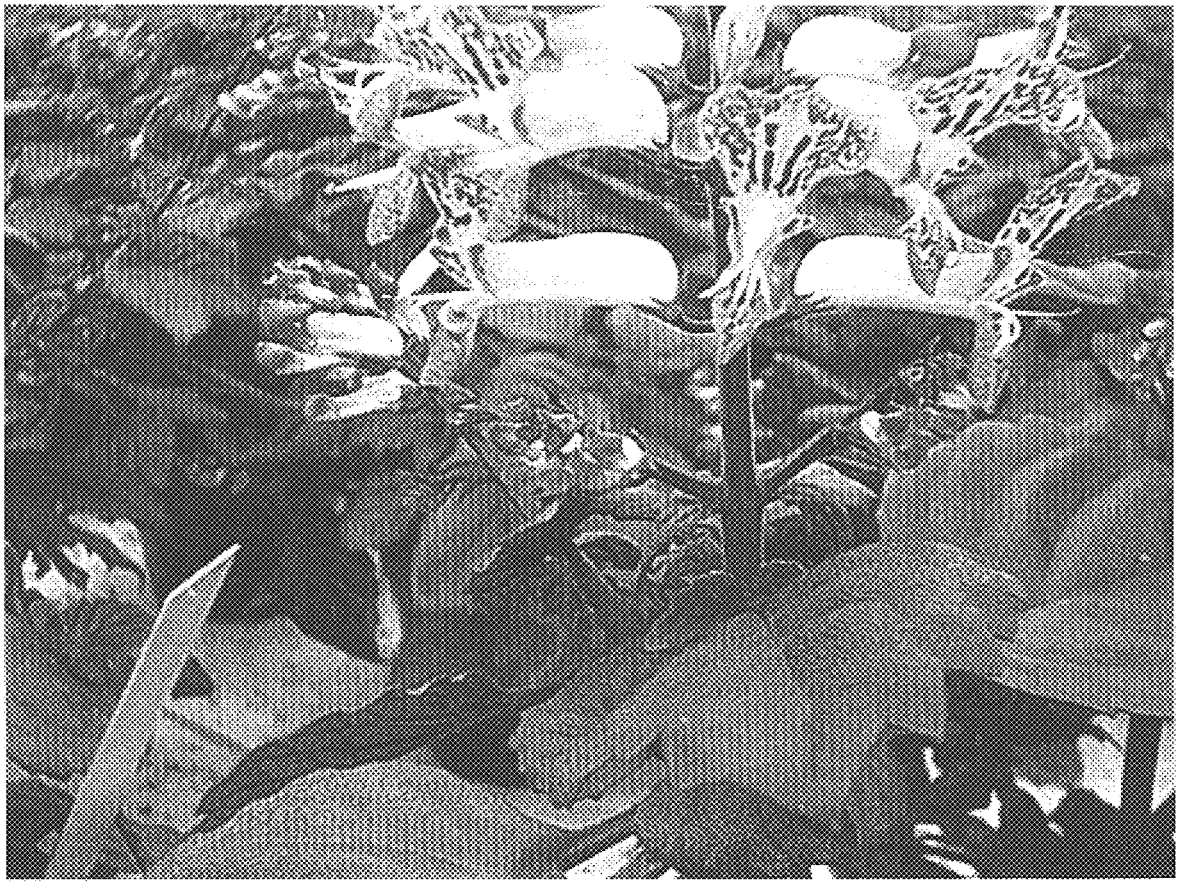

* * * * *